(12) United States Patent
Bonavides et al.

(10) Patent No.: US 9,933,381 B2
(45) Date of Patent: Apr. 3, 2018

(54) DOWNHOLE TOOL FOR DETERMINING ELECTRICAL RESISTANCE OF A FLUID IN A WELLBORE

(71) Applicant: Halliburton Energy Services, Inc., Houston, TX (US)

(72) Inventors: Clovis Satyro Bonavides, Houston, TX (US); Avinash Vinayak Taware, The Woodlands, TX (US); Hua Xia, Huffman, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 15/128,245

(22) PCT Filed: May 27, 2014

(86) PCT No.: PCT/US2014/039553
§ 371 (c)(1),
(2) Date: Sep. 22, 2016

(87) PCT Pub. No.: WO2015/183238
PCT Pub. Date: Dec. 3, 2015

(65) Prior Publication Data
US 2017/0089854 A1    Mar. 30, 2017

(51) Int. Cl.
*G01N 27/08* (2006.01)
*G01N 27/07* (2006.01)
(Continued)

(52) U.S. Cl.
CPC ............ *G01N 27/08* (2013.01); *E21B 49/00* (2013.01); *E21B 49/087* (2013.01); *G01F 1/584* (2013.01);
(Continued)

(58) Field of Classification Search
CPC ........ G01N 27/07; G01N 27/08; G01N 33/18; E21B 2049/085; E21B 47/12;
(Continued)

(56) References Cited

U.S. PATENT DOCUMENTS 4,118,663 A * 10/1978 Barben, II ............. G01N 27/06
324/443
5,574,371 A * 11/1996 Tabanou .................. G01V 3/20
324/324

(Continued)

FOREIGN PATENT DOCUMENTS

| EP | 2191102 | 2/2012 |
|---|---|---|
| GB | 2386691 | 9/2003 |
| WO | 2013147758 | 10/2013 |

OTHER PUBLICATIONS

International Patent Application No. PCT/US2014/039553, "International Search Report and Written Opinion", dated Feb. 17, 2015, 14 pages.

(Continued)

*Primary Examiner* — Jay Patidar
(74) *Attorney, Agent, or Firm* — Kilpatrick Townsend & Stockton LLP (57) ABSTRACT

A measurement assembly for determining an electrical resistance of a fluid in a wellbore is provided. The measurement assembly can include a non-conductive frame, comprising an excitation electrode and a monitoring electrode coupled to the non-conductive frame. The measurement assembly can also include a central electrode in a flow path for the fluid, wherein the flow path is defined by the non-conductive frame. The central electrode can be positioned for conductively coupling the excitation electrode and the monitoring electrode through a conductive path defined by the fluid. Further, the measurement assembly can include a power source for transmitting power to the excitation electrode for (Continued)

determining the electrical resistance of the fluid. The electrical resistance of the fluid can be used to determine whether the fluid includes oil, water, or gas.

18 Claims, 7 Drawing Sheets

(51) Int. Cl.
```
      G01P 5/18       (2006.01)
      G01F 1/712      (2006.01)
      G01F 1/74       (2006.01)
      E21B 49/00      (2006.01)
      E21B 49/08      (2006.01)
      G01F 1/58       (2006.01)
      E21B 47/12      (2012.01)
      G01N 33/24      (2006.01)
```
(52) U.S. Cl.
CPC ........... *G01F 1/712* (2013.01); *G01F 1/74* (2013.01); *G01N 27/07* (2013.01); *G01P 5/18* (2013.01); *E21B 47/12* (2013.01); *E21B 2049/085* (2013.01); *G01N 33/241* (2013.01); *G01N 33/246* (2013.01)

(58) Field of Classification Search
CPC ........ E21B 49/00; E21B 49/087; G01F 1/584; G01F 1/712; G01F 1/74; G01F 1/58; G01P 5/18
USPC ........................................................ 324/324
See application file for complete search history.

(56) References Cited

U.S. PATENT DOCUMENTS

| | | | |
|---|---|---|---|
| 5,736,637 A | 4/1998 | Forgang et al. | |
| 6,369,575 B1* | 4/2002 | Eisenmann | G01V 3/20 324/324 |
| 2003/0080744 A1* | 5/2003 | Goldfine | G01V 3/088 324/345 |
| 2004/0238166 A1 | 12/2004 | Salamitou et al. | |
| 2006/0005965 A1 | 1/2006 | Chouzenoux et al. | |
| 2009/0120637 A1 | 5/2009 | Kirkwood et al. | |
| 2010/0057363 A1 | 3/2010 | Amundsen | |
| 2010/0299068 A1 | 11/2010 | Mason et al. | |
| 2013/0234718 A1* | 9/2013 | Li | G01V 3/24 324/355 |
| 2015/0293254 A1* | 10/2015 | Wang | G01V 3/26 324/355 |
| 2016/0178788 A1* | 6/2016 | Zhang | G01V 3/28 324/324 |

OTHER PUBLICATIONS

GE Oil & Gas, Resistance Array Tool (RAT), available at https://www.geoilandgas.com/sites/geog.dev.local/files/rat_resistance_array_tool.pdf, Jul. 2011, 2 pages.

European Patent Application No. 14893188.4, Extended European Search Report, dated Aug. 4, 2017, 10 pages.

* cited by examiner

DOWNHOLE TOOL FOR DETERMINING ELECTRICAL RESISTANCE OF A FLUID IN A WELLBORE

CROSS-REFERENCE TO RELATED APPLICATIONS

This is a U.S. national phase under 35 U.S.C. 371 of International Patent Application No. PCT/US2014/039553, titled "Downhole Flow-Profiling Tool" and filed May 27, 2014, the entirety of which is incorporated herein by reference.

TECHNICAL FIELD

The present disclosure relates generally to devices for use in well systems. More specifically, but not by way of limitation, this disclosure relates to a tool for downhole flow profiling.

BACKGROUND

A well system (e.g., an oil or gas well) includes a wellbore that is typically drilled for extracting hydrocarbons from a subterranean formation. But not every well system contains enough hydrocarbons to make it commercially viable to continue operating the well. Operators of the well system can determine whether the well system has a commercially productive level of hydrocarbons by analyzing fluid in the wellbore. The characteristics of the fluid (e.g., the multi-phase composition, water-cut, gas/oil ratio, velocity, or flow regime of the fluid) in the wellbore can provide useful information about the viability of the well system.

Fluid in the wellbore, however, can exhibit complex fluid characteristics, for example, a multiphase flow pattern. A multi-phase flow pattern can include at least two fluids with different states (e.g., solids, liquids, or gasses), otherwise referred to as "phases," simultaneously flowing through a medium, for example, the wellbore. Multi-phase flow patterns can include two-phase flow patterns, for example, water-gas or oil-gas flow patterns. Other multi-phase flow patterns can include three-phase (e.g., gas, liquid, and solid), emulsion, turbulent, bubbly, slug, churn, and annular flow patterns. These complex flow patterns and other fluid characteristics can make it challenging to analyze fluid in the wellbore.

DETAILED DESCRIPTION

Certain aspects and features of the present disclosure are directed to a downhole flow-profiling tool. The profiling tool can be positioned in a wellbore. The profiling tool can include a non-conductive frame (hereinafter a "frame"). That is, the frame may not be electrically conductive. One or more excitation electrodes and one or more monitoring electrodes can be coupled to the frame. In some embodiments, the frame can include a ring shape. The one or more excitation electrodes and one or more monitoring electrodes can be coupled to the ring-shaped frame. In other embodiments, the frame can include a cylindrical shape. The one or more excitation electrodes and the one or more monitoring electrodes can be coupled to the inside of the cylindrically-shaped frame. In some embodiments, the frame can include multiple rails (i.e., rods) configured to form a cylindrical or grid shape. The one or more excitation electrodes and the one or more monitoring electrodes can be coupled to multiple rails. A frame that includes a set of one or more excitation electrodes conductively coupled to one or more monitoring electrodes will hereinafter be referred to as a "ring."

The profiling tool can also include a central electrode positioned in the cross-section of the ring (or frame). In some embodiments, the central electrode can be positioned in the cross-sectional center of the ring. In some embodiments, the central electrode can be positioned on a non-conductive rail (i.e., a non-conductive rod). The non-conductive rail can be suspended in the cross-section of the ring.

Fluid (e.g., from inside the wellbore) can flow through the ring (or frame). The fluid can include a mixture of different fluids, for example, a mixture of oil, water, and gas. Further, the different fluids can have different electrical properties (e.g., different resistances).

The profiling tool can be used to determine the electrical resistances (hereinafter "resistances") of the different fluids in the fluid mixture. To determine the resistances of the different fluids in the fluid mixture, multiple pulses of power can be transmitted (e.g., by a power source such as a battery) to one or more of the excitation electrodes coupled to the ring. In some embodiments, each pulse of power can have the same amount of power (e.g., voltage) but can be transmitted to different combinations of excitation electrodes. In other embodiments, each pulse of power can have a different amount of power, but can be transmitted to the same combination of excitation electrodes.

For each pulse of power transmitted to the one or more excitation electrodes, current can flow from an excitation electrode, through the fluid, and to the central electrode. The current can then flow back through the fluid, to a monitoring electrode, and back to the excitation electrode. This creates a series of current loops across the cross-sectional plane of the electrodes, which can be represented as linear equations using Kirchhoff's Voltage Law. The resistances of the different fluids in the fluid mixture can be unknown variables in the linear equations. Further, during each pulse of power, the current and voltage can be measured at each excitation electrode, and the voltage can be measured at each monitoring electrode. The currents coming into and going out of each excitation electrode can be represented using Kirchoff's current law. The measured currents and voltages can be known variables in the linear equations formed by applying Kirchhoff's voltage and current laws.

In some embodiments if a sufficient number of pulses of varying power are applied to the same excitation electrodes, the linear equations that have known voltages and currents, and unknown resistances and unknown currents, can be solved. In other embodiments, if a sufficient number of pulses of the same power are applied to different sets of excitation electrodes, the linear equations that have known voltages and currents, and unknown resistances and unknown currents, can be solved. Solving the linear equations can yield solutions for the resistances of the different fluids in the fluid mixture. Based on the determined resistances of the different fluids in the fluid mixture, additional information about the different fluids (e.g., the velocity, flow regime, volumetric flow rate, mass flow rate, or composition of the different fluids) can be determined.

In some embodiments, the profiling tool can include multiple rings with a central electrode positioned in the cross-section of each ring. The rings can be coupled to non-conductive rails for stability and positioned with their cross-sections aligned. In some embodiments, the rings can be arranged in multiple sets. For example, in one embodiment, the profiling tool includes two sets of rings, where each set of rings includes three rings. The set of rings can include a guard ring, a measurement ring, and another guard ring, respectively. The measurement ring is structurally identical to, and functions the same as, the ring described above. That is, the measurement ring can be used to determine resistances associated with the fluid flowing through the set of rings. The guard rings can be substantially structurally identical to the rings described above. The guard rings, however, may not be used to determine resistances associated with the fluid flowing through the set of rings. Rather, the guard rings can limit the flow of current in the measurement ring to the cross-sectional plane of the measurement ring, as described below.

In some embodiments, multiple pulses of power can be transmitted to all of the rings in the set of rings (e.g., the guard rings and the measurement ring) substantially simultaneously. The pulses of power transmitted to the all of the rings in the set of rings can have the same characteristics. That is, the pulses of power can have the same amount of power and can be transmitted to the same combination of excitation electrodes coupled to each ring. This can result in all of the rings in the set of rings having substantially equal electrical potential levels. If all the rings in the set of rings have substantially equal electrical potential levels, current may not flow between the measurement ring and the guard rings. Rather, the current applied to the measurement ring may substantially flow in the cross-sectional plane of the measurement ring. Limiting the current flow to the cross-sectional plane of the measurement ring can improve the accuracy of the voltages and currents measured from the measurement ring during each pulse of power. Improving the accuracy of the voltage and current measurements can improve the accuracy of the resistance values determined from the voltage and current measurements (and thus the accuracy of any fluid information determined based on the resistances).

In some embodiments, the multiple rings or multiple sets of rings can be operated in sequence or in concert to obtain multiple sets of resistance values for the fluid flowing through the rings. Additional information about the fluid can be determined based on the multiple sets of resistance values. For example, the resistance values can be analyzed (e.g., using statistical correlation techniques) to determine the velocity of the fluids. Additionally, in some embodiments, the resistance values can be used to graphically model the fluid's characteristics in the space and time domains, for example, as a fluid velocity distribution map. Graphical models of the fluid's characteristics can provide useful information to well operators.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

Figure 1:
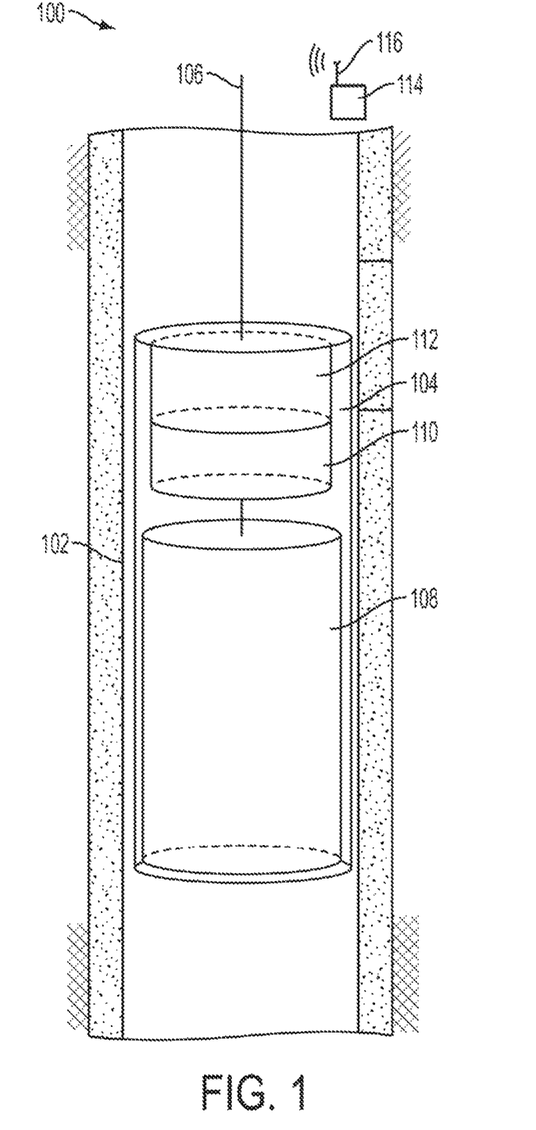
FIG. 1 is a cross-sectional side view of one embodiment of a wellbore system with a downhole flow-profiling tool according to one aspect of the present disclosure.

FIG. 1 is a cross-sectional side view of one embodiment of a wellbore system 100 with a downhole flow-profiling tool 108 according to one aspect of the present disclosure. In this example, the wellbore system 100 can be for extracting oil or gas from a subterranean formation. The wellbore system 100 can include a wellbore 102. In some embodiments, the wellbore 102 can be cased and cemented, as shown in FIG. 1. In other embodiments, the wellbore 102 can be uncased or the casing may not be cemented. In some embodiments, the wellbore system 100 can be in its production stage.

Figure 2:
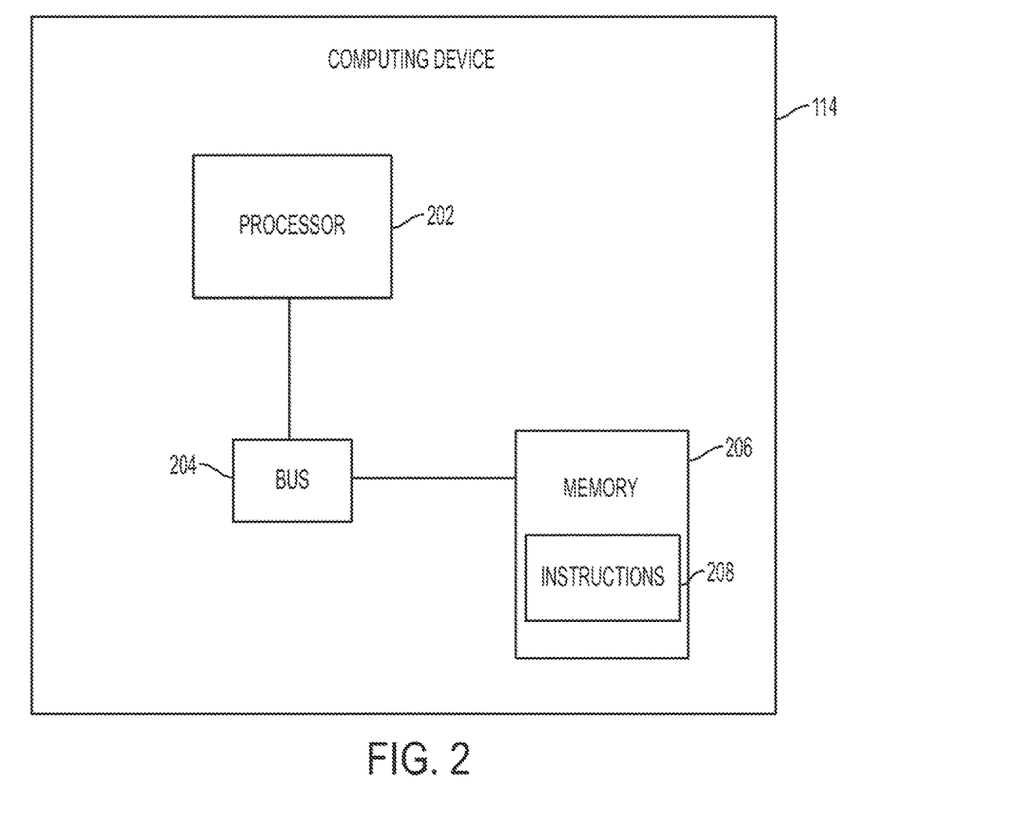
FIG. 2 is a block diagram depicting an example of a computing device for use with a downhole flow-profiling tool according to one aspect of the present disclosure.

The wellbore system 100 can also include a computing device 114. The computing device 114 can determine a characteristic of a fluid in the wellbore 102 based on data from a logging tool 104 in the wellbore 102. The computing device 114 can be positioned at the surface of the wellbore 102, below ground, or offsite. As shown in FIG. 2, the computing device 114 can include a processor 202 interfaced with other hardware via a bus 204. A memory 206, which can include any suitable tangible (and non-transitory) computer-readable medium such as RAM, ROM, EEPROM, or the like, can embody program components (e.g., instructions 208) that configure operation of the computing device 114. The computing device 114 can also include input/output interface components (e.g., for interfacing with a display, a keyboard, or a mouse) and additional storage.

Returning to FIG. 1, the computing device 114 can further include a communication device 116 for transmitting data to and receiving data from the logging tool 104. The communication device 116 can represent one or more of any components that facilitate a network connection. In this example, the communication device 116 is wireless and can include wireless interfaces such as IEEE 802.11, Bluetooth, or radio interfaces for accessing cellular telephone networks (e.g., transceiver/antenna for accessing a CDMA, GSM, UMTS, or other mobile communications network). In other embodiments, the communication device 116 can be wired and can include interfaces such as Ethernet, USB, or IEEE 1394.

The wellbore system 100 can include the logging tool 104. The logging tool 104 can include one or more instruments (e.g., the profiling tool 108). The instruments can determine the characteristics of the wellbore 102, the fluid within the wellbore 102, or the formation (e.g., the physical makeup of the formation, or its electrical, acoustic, or electromagnetic properties). In some embodiments, the logging tool 104 can be suspended in the wellbore 102 on a wireline 106, a slickline, or a coiled tube, or can be included in a bottom hole assembly or pipe-conveyed tools. In some embodiments, various instruments can be suspended within the logging tool 104 on a wireline 106.

The logging tool 104 can include a telemetry unit 112. The telemetry unit 112 can communicate data between the logging tool 104 and the computing device 114 (via the communication device 116). In some embodiments, the telemetry unit 112 can communicate data between the logging tool 104 and the computing device 114 via a wired interface, such as wireline 106, or a wireless interface. In some embodiments, the telemetry unit 112 can be configured substantially the same as the communication device 116.

The logging tool 104 can also include an electronics unit 110. The electronics unit 110 can operate or transmit power to one or more other components (e.g., the telemetry unit 112 or the profiling tool 108) in the logging tool 104. The electronics unit 110 can include a power source. In some embodiments, the electronics unit 110 can transmit data to, and receive data from, other components in the logging tool 104. Further, in some embodiments, the electronics unit 110 can include a computing device, which can be configured similar to the computing device 114 shown in FIG. 2.

The logging tool 104 further includes a profiling tool 108. The profiling tool 108 can be used to determine a characteristic of a fluid flowing through the profiling tool 108 (i.e., in the wellbore 102). Although depicted in FIG. 1 as separate from the electronics unit 110 and the telemetry unit 112, in some embodiments, the profiling tool 108 can include the electronics unit 110 or the telemetry unit 112.

The electronics unit 110 can operate the profiling tool 108 to determine information about a fluid flowing through the profiling tool 108. In some embodiments, the electronics unit 110 operates the profiling tool in response to commands sent from the computing device 114. The electronics unit 110 can operate the profiling tool 108 by transmitting power to excitation electrodes within the profiling tool 108 (discussed further with respect to FIG. 5). During each power transmission, the electronics unit 110 can measure voltages and currents at locations within the profiling tool 108.

In some embodiments, based on the voltage measurements and the current measurements, the electronics unit 110 can determine resistances associated with the fluid flowing through the profiling tool 108. Based on the determined resistances, the electronics unit 110 can determine information about the fluid (e.g., the composition, velocity, or flow regime of the fluid) that may be important to well operators. Further, the electronics unit 110 can transmit the determined information (via the telemetry unit 112) to the computing device 114.

In other embodiments, rather than performing the above resistance and information determinations in the wellbore 102, the electronics unit 110 can transmit the voltage measurements and current measurements, via the telemetry unit 112, to the computing device 114. Based on the voltage measurements and the current measurements, the computing device 114 can determine the resistances associated with the fluid flowing through the profiling tool 108. Based on the determined resistances, the computing device 114 can determine information about the fluid (e.g., the composition, velocity, or flow regime of the fluid) that may be important to well operators.

Figure 3:
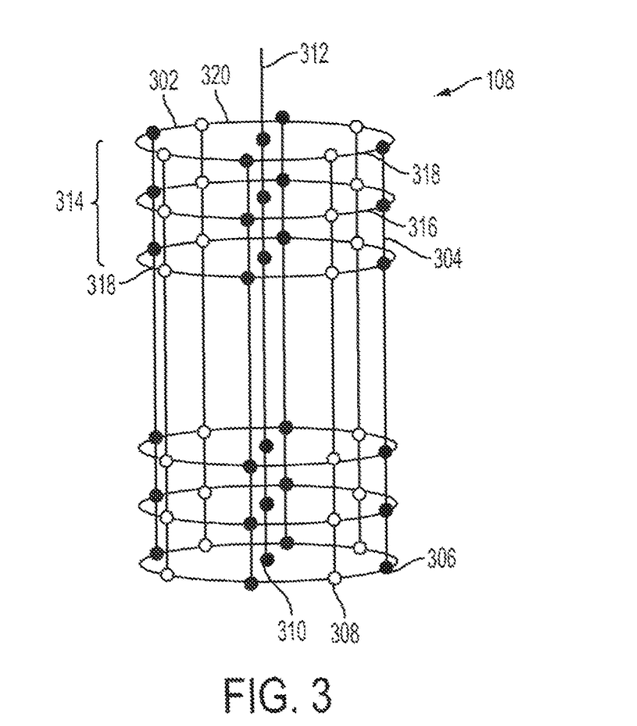
FIG. 3 is a side model view of the downhole flow-profiling tool shown in FIG. 1.

FIG. 3 is a side model view of the downhole flow-profiling tool shown in FIG. 1. In this embodiment, the profiling tool 108 includes multiple rings 302. As described above, the rings 302 can include a frame 320 that can be non-conductive. In some embodiments, the frame 320 can include a ring shape. Each ring 302 can include one or more excitation electrodes 306 and one or more monitoring electrodes 308 coupled to the frame 320. Further, in some embodiments, the rings 302 can be connected to one or more rails 304. The rails 304 can provide stability to the profiling tool 108. The rails 304 can include any insulating material, for example plastic, for electrically insulating the rings 302 from each other. In other embodiments, the frame 320 can include a cylindrical shape. In such embodiments, the one or more excitation electrodes 306 and one or more monitoring electrodes 308 can be coupled to the interior of the cylindrically-shaped frame.

Figure 8:
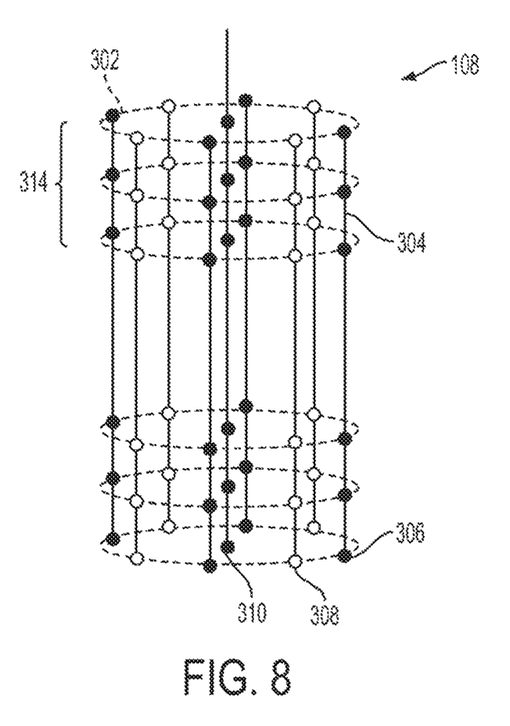
FIG. 8 a side model view of another embodiment of the downhole flow-profiling tool shown in FIG. 1.
Figure 9:
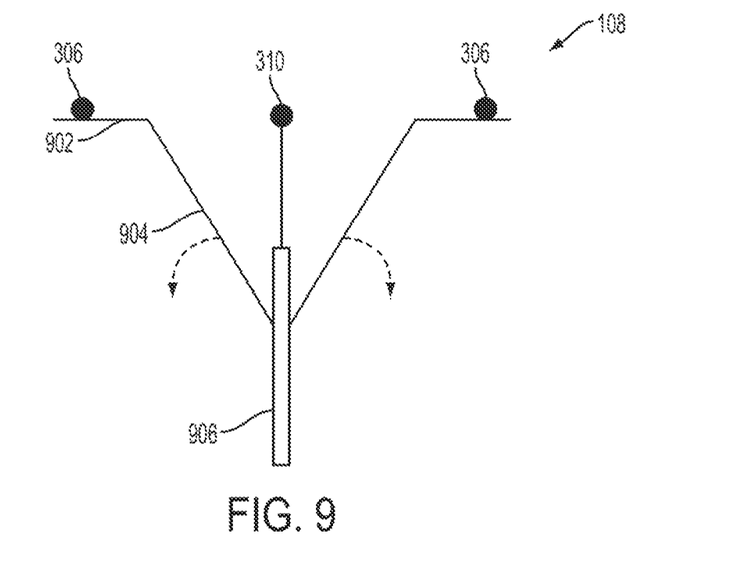
FIG. 9 is a cross-sectional side view of still another embodiment of the downhole flow-profiling tool shown in FIG. 1.

In some embodiments, the ring 302 may not include the frame 320. For example, in the embodiment shown in FIG. 8, the ring 302 can include a frame comprising only the rails 304, which can be configured in a substantially cylindrical shape. Another example frame configuration is shown FIG. 9. In the embodiment shown in FIG. 9, one or more excitation electrodes 306 and one or more monitoring electrodes (not shown for simplicity) are each coupled to a pad 902. Each pad 902 can be coupled to a retractable rail 904 (e.g., rods). In other embodiments, the one or more excitation electrodes 306 and one or more monitoring electrodes can be directly coupled to the retractable rail 904 without the pad 902. The retractable rails 904 can be rotatably coupled to a base component 906. By rotating or pivoting the retractable rails 904 in relation to the base component 906, the diameter of the ring created by the one or more excitation electrodes 306 and one or more monitoring electrodes can increase or decrease. A central excitation electrode 310 can be coupled to the base component 906. Although only two excitation electrodes 306, two retractable rails 904, two pads 902, and no monitoring electrodes are shown in FIG. 9 for simplicity, in other embodiments, there can be any number of excitation electrodes 306, retractable rails 904, pads, and monitoring electrodes.

Returning to FIG. 3, in some embodiments, the rings 302 can be grouped into sets of rings 314. There can be any number of sets of rings 314 in the profiling tool, and the sets of rings 314 can be positioned at any distance from one another. In this example, there are two sets of rings 314, and each set of rings 314 includes three rings. The three rings 302 can include two guard rings 318 and one measurement ring 316. The guard rings 318 and the measurement ring 316 can have substantially identical structures and can function in substantially similar ways. The purpose of the guard rings 318 will be discussed further with respect to FIG. 6.

Further, as described above, a central electrode 310 can be positioned inside the cross-section of each ring 302. For example, in some embodiments, the central electrode 310 can be positioned in the cross-sectional center of each ring 302. In some embodiments, the central electrode 310 can be positioned in the cross-section of the ring 302 via a central rail 312. The central rail 312 can include any insulating material, for example a plastic or fiber glass, for electrically insulating the central electrodes 310 from each other.

Figure 4:
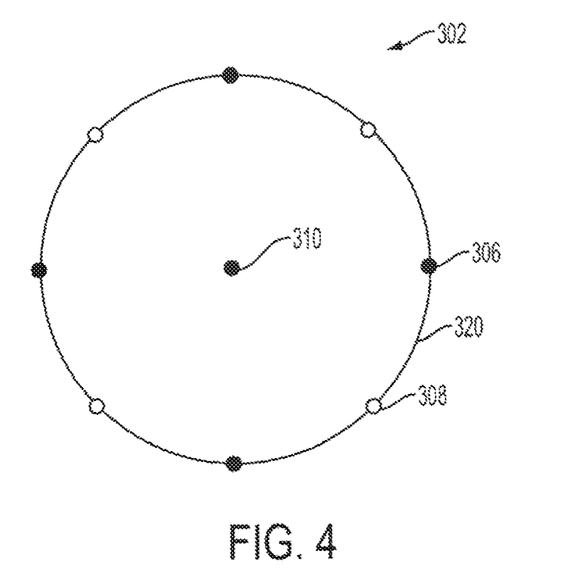
FIG. 4 is a cross-sectional end view of a ring in the downhole flow-profiling tool shown in FIG. 3.

FIG. 4 is a cross-sectional end view of a ring 302 in the downhole flow-profiling tool 108 shown in FIG. 3. As noted above, the ring 302 can include one or more excitation electrodes 306 and one or more monitoring electrodes 308. In this example, the ring 302 includes four excitation electrodes 306 and four monitoring electrodes 308. The excitation electrodes 306 can include a conductive material, for example, copper, tin, iron, silver, gold, or lead. The monitoring electrodes 308 can include a material with high electrical impedance, for example, a resistor.

In some embodiments, the ring 302 can include a frame 320. In other embodiments (e.g., the embodiment shown in FIG. 8), the ring 302 may not include the frame 320. The frame 320 can include a non-conductive material or an insulating material, for example, plastic or fiberglass. In some embodiments, the frame 320 can be configured to position the excitation electrodes 306 and the monitoring electrodes 308 in a substantially circular shape. For example, the frame 320 can be curved such that the frame 320 has a circular shape, a ring shape, or a cylindrical shape. In other embodiments, the frame 320 can be configured such that the frame 320 has a different shape, for example, a square shape.

A central electrode 310 can be positioned (e.g., via a non-conductive rail) in the cross-section of the ring 302 (or frame 320). The central electrode 310 can include a conductive material, for example, copper, tin, iron, silver, gold, or lead. In some embodiments, the central electrode 310 can have the same electrical properties (e.g., be of the same type as) as the excitation electrodes 306.

Figure 5:
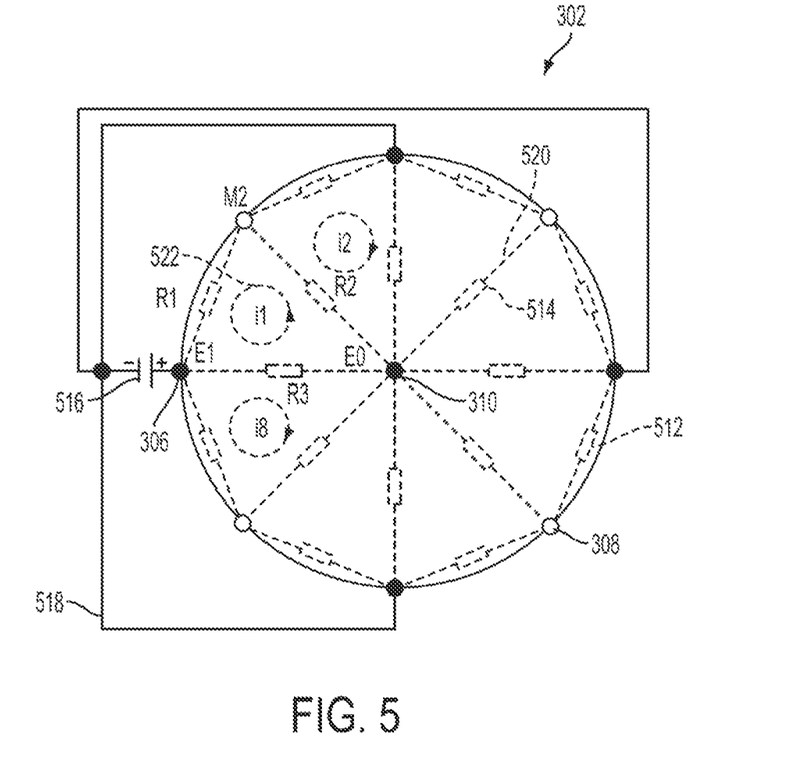
FIG. 5 is a schematic view of the ring shown in FIG. 4.

FIG. 5 is a schematic view of the ring 302 shown in FIG. 4. A fluid can flow through the cross-section of the ring 302. The fluid can include a mixture of different fluids, for example, a mixture of oil, water, and gas. The different fluids in the fluid mixture can flow through different cross-sectional areas of the ring 302 at any given instant in time.

Further, fluids can have electrical properties (e.g., a conductance and a resistance), and the different fluids in the fluid mixture can have different electrical properties (e.g., water is more conductive than oil, and oil is more conductive than gas). Thus, each of the different fluids in the fluid mixture can be represented as a conductor 520 coupled to a resistor 514, where the resistance of the resistor 514 varies depending on the type of fluid.

A power source 516 (e.g., from within the electronics unit) can transmit a pulse of power via a conductor 518 (e.g., a wire or rail) to one or more excitation electrodes 306. The conductor 518 can include any conductive material, for example, copper, tin, iron, silver, gold, or lead. A pulse of power transmitted by the power source 516 to one or more excitation electrodes 306 can be an "excitation." In some embodiments, the power source 516 can transmit a different amount of power to the same combination of excitation electrodes 306 for each excitation. In other embodiments, the power source 516 can transmit the same amount of power to different combinations of excitation electrodes 306 for each excitation. The number of different combinations of excitation electrodes 306 to which the power source 516 can transmit power can be represented as N(N−1), where N is the number of excitation electrodes 306 in the ring 302. Thus, in this example, because there are five excitation electrodes 306, there can be up to 20 different combinations of excitation electrodes 306 to which the power source 516 can transmit power. The power source 516 can transmit power to the different combinations of excitation electrodes 306 via switching circuitry, which can be a part of the electronics unit. The switching circuitry can include, for example, a relay, a switch, a processor, a microcontroller, or a multiplexer.

Further, during each excitation, the electronics unit can measure the amount of voltage and the amount of current at each excitation electrode 306. The electronics unit can also measure the amount of voltage at each monitoring electrode 308. In some embodiments, the speed of each excitation (and the associated current and voltage measurements) can be faster than the amount of time it takes for the fluid to flow through the ring 302. For example, each excitation can have duration of less than 10 μs, which can be faster than the amount of time it takes for the fluid to flow through the ring 302.

During an excitation, if the central electrode 310 is at a lower electrical potential level than an excitation electrode 306, current can flow from the excitation electrode 306 through the fluid to the central electrode 310. The current can then flow from the central electrode 310 back through the fluid to a monitoring electrode 308. Because the monitoring electrode 308 can have a high impedance, the current can then flow from the monitoring electrode 308 through the fluid (which has a resistance depicted by resistor 512) back to the excitation electrode 306. Thus, the current flow creates a current loop 522 in each "slice" or "sector" of the ring 302. In this example, because there can be eight total "slices" in the ring 302, there can be eight total current loops within the ring 302. Further, in this example, there can be three additional current loops outside of the ring 302, resulting from the conductors 518 and the excitation electrodes 306 to which the conductors 518 are coupled. Thus, there can be 11 total current loops in this example. Only three current loops 522 (i.e., i1, i2, and i8) are shown in this example, however, for clarity.

The electrical characteristics of each of the 11 current loops can be represented as a linear equation using Kirchhoff's Voltage Law. For example, the electrical characteristics associated with current loop i1 can be represented as:

$$i1(R1)+(i1-i2)R2+(i1-i8)R3+V_{E1}+V_{M2}+V_{E0}=0$$

where i1 is the current in current loop i1, i2 is the current in current loop i2, i8 is the current in current loop i8, R1 is the resistance of resistor R1, R2 is the resistance of resistor R2, R3 is the resistance of resistor R3, $V_{E1}$ is the voltage at excitation electrode E1, $V_{M2}$ is the voltage at monitoring electrode M2, and $V_{E0}$ is the voltage at central electrode E0. Because there are 11 total current loops, there can be 11 total linear equations.

The equations can include 11 total unknown current values because of the 11 current loops. The equations can also include 16 total unknown resistance values (i.e., from resistors 512 and 514). Because the power source 516 can apply multiple excitations to the ring 302 faster than the than the amount of time for the fluid to flow through the ring 302, the unknown resistance values can remain constant between excitations. Thus, the total number of unknown variables in the equations can be represented as 16+11*n, where n is the number of excitations.

Further, in this example, because the voltage at each of the four excitation electrodes 306, the one central electrode 310, and the four monitoring electrodes 308 can be measured for each excitation, a total of nine known voltages can be determined. Also, because the current at each of the four excitation electrodes 306 and the one central electrode 310 can be measured for each excitation, a total of five known currents can be determined. Therefore, the total number of known variables in the equations can be represented as 14*n. Table 1 depicts the number of known variables and the number of unknown variables in the equations based on the number of excitations applied to the ring 302:

TABLE 1

| Excitation number (n) | Number of Known Variables (14 * n) | Number of Unknown Variables (16 + 11 * n) |
| --- | --- | --- |
| 1 | 14 | 27 |
| 2 | 28 | 38 |
| 3 | 42 | 49 |
| 4 | 56 | 60 |
| 5 | 70 | 71 |
| 6 | 84 | 82 |
| 7 | 98 | 93 |

As shown in Table 1, as the number of excitations increases, the number of known variables can become greater than the number of unknown variables in the equations (i.e., the system of linear equations can become "over-determined"). In this example, after six excitations, the number of known variables becomes greater than the number of unknown variables. Upon the number of known variables exceeding the number of unknown variables, the equations can be solved for the values of the unknown resistances.

As the number of excitations continues to increase, the degree of over-determination of the system of linear equations increases. A higher degree of over-determination can result in more accurate resistance values. In some embodiments, a statistical analysis can be performed on the solved resistance values to determine more accurate resistance values. For example, in one embodiment, a least-squares analysis for over-determined linear systems can be performed on the solved resistance values to determine more accurate resistance values.

The resistance values can be used to determine one or more characteristics of the fluid flowing through the ring 302. For example, in some embodiments, the resistance values can be correlated with their associated fluid types (e.g., oil, water, or gas) via a lookup table. Thus, based on the resistance values, the composition of the fluid (e.g., if the fluid contains oil, water, or gas, or a combination thereof) flowing through the ring 302 can be determined.

In some embodiments, the resistance values can be used to determine the quantities of the different fluids in the fluid mixture flowing through the ring 302. For example, in some embodiments, each resistance value can be associated with a "slice" of the cross-section of the ring 302, with each "slice" taking up a predetermined geometric area of the cross-section of the ring 302. Based on the number of "slices" of the ring 302 associated with a particular type of fluid in the fluid mixture, the quantity of the particular fluid can be determined. For example, in some embodiments, the quantity of the particular fluid can be determined by multiplying the total number of slices associated with the particular fluid by the area of each slice.

Further, in some embodiments, there can be two or more rings 302 in the profiling tool (e.g., as shown in FIG. 3). The resistances associated with the fluid can be determined via the two or more rings 302. The resistances associated with the fluid determined from the two or more rings 302 can be compared (e.g., using statistical correlation techniques) to determine additional information about the fluid. For example, in some embodiments, the amount of time it takes for the fluid to pass from one ring 302 in the profiling tool to another ring 302 can be used to determine the velocity of the fluid. The resistances associated with the fluid can be further analyzed to determine, for example, the flow regime (e.g., laminar or turbulent), the mass flow rate, or the volumetric flow rate of the fluid.

In some embodiments, increasing the number of excitation electrodes 306 or monitoring electrodes 308 can increase the resolution of the profiling tool. For example, increasing the number of excitation electrodes 306 and monitoring electrodes 308 can increase the number of "slices" around the cross-section of the ring 302. As the number of "slices" increases, the number of unknown resistances and linear equations associated with the ring 302 can increase. Upon solving the increased number of linear equations for the increased number of unknown resistances, a more detailed level of information about the fluid flowing through the ring 302 can be determined.

In some embodiments, the electronics unit can transmit data (e.g., the resistances, composition, velocity, or flow regime) associated with the fluid to a computing device, as described with respect to FIG. 1. The computing device can output the data textually or as a graphical representation via a display. In some embodiments, the graphical representation can depict the data using different shapes, colors, or color intensities (e.g., as a fluid velocity distribution map). For example, in some embodiments, the computing device can output a cross-sectional image of a ring 302 via the display. The cross-sectional image of the ring 302 can include blue zones, brown zones, and yellow zones associated with where water, oil, and gas, respectively, are flowing through the cross-section of the ring 302. If the data can be determined at a high enough speed (e.g., higher than 30 times per second), in some embodiments, the graphical representation can be animated. Static and animated graphical representations of data associated with the fluid in a wellbore can provide valuable visual aids to well operators.

Figure 6:
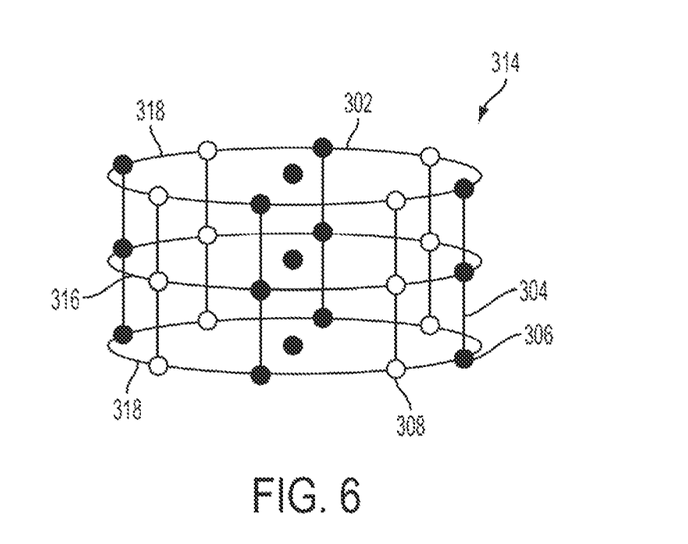
FIG. 6 is a side view of one of the sets of rings in the downhole flow-profiling tool shown in FIG. 3.

FIG. 6 is a side view of one of the sets of rings 314 in the downhole flow-profiling tool 108 shown in FIG. 3. In this example, the set of rings 314 includes two guard rings 318 and one measurement ring 316. As noted above, the guard rings 318 and the measurement ring 316 have substantially similar structures. The guard rings 318 can be equidistant from the measurement ring 316.

In some examples, all of the rings 302 can be excited substantially simultaneously with the same amount of power and via the same electrode combinations. Exciting the rings 302 with the same amount of power and via the same electrode combinations can result in the rings 302 having substantially equal electrical potential levels. That is, the voltage difference between the rings 302 can be zero. If the rings 302 have substantially equal electrical potential levels, current may not flow between the rings 302. Thus, the flow of current in the measurement ring 316 can be restricted to the current loops in the cross-sectional plane of the measurement ring 316 (described with respect to FIG. 5). This can improve the accuracy of the voltage and current measurements taken at the excitation electrodes 306, and the voltage measurements taken at the monitoring electrodes 308, during each excitation of the measurement ring 316. The improved voltage and current measurements can result in more accurate resistance values being derived from the system of linear equations associated with the measurement ring 316. More accurate resistance values can result in more accurate determinations about the characteristics of the fluid flowing through the measurement ring 316.

Figure 7:
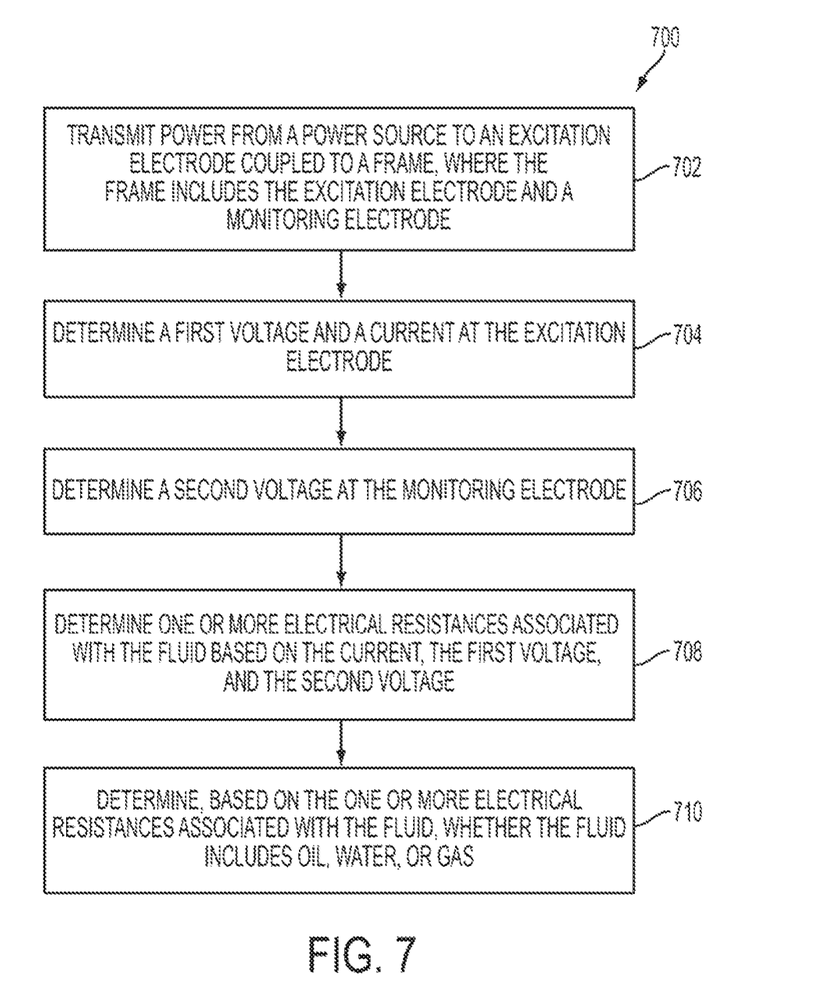
FIG. 7 is an example of a flow chart of a process for using a downhole flow-profiling tool according to one embodiment.

FIG. 7 is an example of a flow chart of a process for using a downhole flow-profiling tool according to one embodiment.

In block 702, a power source transmits power to an excitation electrode coupled to a ring. The ring can include one or more excitation electrodes and one or more monitoring electrodes coupled to a frame. A central electrode can be positioned, for example within the cross-section of the frame, for conductively coupling the excitation electrode and the monitoring electrode through a conductive path defined by a fluid. Current can flow from the one or more excitation electrodes, through the fluid to the central electrode, back through the fluid to the one or more monitoring electrodes, and back through the fluid to the excitation electrodes.

In block 704, an electronics unit determines a voltage and a current at the excitation electrode. The electronics unit can include analog or digital circuitry for determining the voltage and the current.

In block 706, the electronics unit determines a voltage at the monitoring electrode. The electronics unit can include analog or digital circuitry for determining the voltage.

In block 708, a computing device determines one or more resistances associated with the fluid flowing through the ring. The resistances can be determined based on the voltage and current measurements at the excitation electrode, and the voltage measurement at the monitoring electrode. The voltage and current measurements at the excitation electrode, and the voltage measurement at the monitoring electrode, can be applied to a system of linear equations representing the electrical properties of the ring (i.e., the excitation and monitoring electrodes coupled to the ring, and the fluid flowing through the ring). The computing device can solve the system of linear equations to determine the resistances.

In block 710, the computing device determines, based on the resistances associated with the fluid, whether the fluid includes oil, water, or gas. In some embodiments, the computing device can determine if the fluid includes additional kinds of fluids.

In some aspects, an assembly for downhole flow-profiling tool is provided according to one or more of the following examples.

Example #1

A measurement assembly for determining an electrical resistance of a fluid in a wellbore can include a non-conductive frame. The non-conductive frame can include an excitation electrode and a monitoring electrode coupled to the non-conductive frame. The assembly can also include a central electrode in a flow path for the fluid. The flow path can be defined by the non-conductive frame. The central electrode can be positioned for conductively coupling the excitation electrode and the monitoring electrode through a conductive path defined by the fluid. The assembly can further include a power source for transmitting power to the excitation electrode for determining the electrical resistance of the fluid. The electrical resistance of the fluid can be used to determine whether the fluid includes oil, water, or gas.

Example #2

The assembly of Example #1 may feature the electrical resistance being usable to determine a composition, a flow velocity, a quantity of a fluid component, and a flow regime of the fluid.

Example #3

The assembly of any of Examples #1-2 may feature the non-conductive frame including a ring shape or a cylindrical shape.

Example #4

The assembly of any of Examples #1-3 may feature multiple non-conductive frames and multiple central electrodes.

Example #5

The assembly of Example #4 may feature the multiple non-conductive frames being coupled to multiple rails and the multiple central electrodes being couple to a central rail.

Example #6

The assembly of Example #5 may feature the each of the multiple rails and the central rail including an insulator.

Example #7

The assembly of any of Examples #4-6 may feature the multiple non-conductive frames including two sets of rings. Each of the two sets of rings can include two guard rings and a measurement ring.

Example #8

The assembly of Example #7 may feature the two guard rings being equidistant from the measurement ring.

Example #9

The assembly of any of Examples #1-8 may feature multiple excitation electrodes and multiple monitoring electrodes.

Example #10

The assembly of any of Examples #1-9 may feature an electronics unit and a telemetry unit.

Example #11

An assembly for determining an electrical resistance of a fluid in a wellbore can include excitation electrodes and monitoring electrodes coupled to a non-conductive frame. Fluid flowing through the non-conductive frame can provide a conductive path for conductively coupling the excitation electrodes and the monitoring electrodes. The assembly can also include a central electrode positioned in a cross-sectional center of the non-conductive frame. The central electrode can be positioned for conductively coupling the excitation electrodes and the monitoring electrodes through another conductive path defined by the fluid. The assembly can further include a power source for exciting one or more of the excitation electrodes for determining the electrical resistance of the fluid. The electrical resistance of the fluid can be used to determine whether the fluid includes oil, water, or gas.

Example #12

The assembly of Example #11 may feature the electrical resistance being further usable to determine a composition, a flow velocity, a quantity of a fluid component, and a flow regime of the fluid.

Example #13

The assembly of any of Examples #11-12 may feature multiple non-conductive rings and multiple central electrodes.

Example #14

The assembly of Example #13 may feature the multiple non-conductive rings being coupled to multiple rails and the multiple central electrodes being coupled to a central rail.

Example #15

The assembly of Example #14 may feature the each of the multiple rails and the central rail including an insulator.

Example #16

The assembly of any of Examples #13-15 may feature the multiple non-conductive rings including two sets of rings. Each of the two sets of rings can include two guard rings and a measurement ring.

Example #17

The assembly of Example #16 may feature the two guard rings being equidistant from the measurement ring.

Example #18

A method can include transmitting power from a power source to an excitation electrode couple to a non-conductive frame. The non-conductive frame can include the excitation electrode and a monitoring electrode. A central electrode can be positioned for conductively coupling the excitation electrode and the monitoring electrode through a conductive path defined by a fluid. The method can also include determining, by an electronics unit, a current and a first voltage at the excitation electrode. The method can further include determining, by the electronics unit, a second voltage at the monitoring electrode. The method can also include determining, by a computing device, one or more electrical resistances associated with the fluid based on the current, the first voltage, and the second voltage. Finally, the method can include determining, by the computing device and based on the one or more electrical resistances associated with the fluid, whether the fluid includes oil, water, or gas.

Example #19

The method of Example #18 may feature determining, by the computing device, a composition, a flow velocity, a quantity of a fluid component, and a flow regime of the fluid.

Example #20

The method of any of Examples #18-19 may feature transmitting, by a telemetry unit, the current, the first voltage, and the second voltage from the electronics unit to the computing device.

The foregoing description of certain embodiments, including illustrated embodiments, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A measurement assembly for determining an electrical resistance of a fluid in a wellbore, comprising:
   a non-conductive frame comprising an excitation electrode and a monitoring electrode coupled to the non-conductive frame, wherein an interior of the non-conductive frame defines a flow path through which the fluid is to flow;
   a central electrode in the flow path for the fluid, wherein the central electrode is positioned for conductively coupling the excitation electrode and the monitoring electrode through a conductive path defined by the fluid; and
   a power source for transmitting power to the excitation electrode for determining the electrical resistance of the fluid.

2. The measurement assembly of claim 1, wherein the non-conductive frame comprises a ring shape or a cylindrical shape.

3. The measurement assembly of claim 1, further comprising a plurality of non-conductive frames and a plurality of central electrodes.

4. The measurement assembly of claim 3, wherein the plurality of non-conductive frames are coupled to a plurality of rails and the plurality of central electrodes are coupled to a central rail.

5. The measurement assembly of claim 4, wherein each of the plurality of rails and the central rail comprises an insulator.

6. The measurement assembly of claim 3, wherein the plurality of non-conductive frames comprises two sets of rings, and wherein each of the two sets of rings comprises two guard rings and a measurement ring.

7. The measurement assembly of claim 6, wherein the two guard rings are equidistant from the measurement ring.

8. The measurement assembly of claim 1, further comprising a plurality of excitation electrodes and a plurality of monitoring electrodes.

9. The measurement assembly of claim 1, further comprising an electronics unit and a telemetry unit.

10. An assembly for determining an electrical resistance of a fluid in a wellbore, comprising:
    excitation electrodes and monitoring electrodes coupled to a non-conductive frame, wherein fluid flow through an interior of the non-conductive frame provides a conductive path for conductively coupling the excitation electrodes and the monitoring electrodes;
    a central electrode positioned in a cross-sectional center of the non-conductive frame, wherein the central electrode is positioned for conductively coupling the excitation electrodes and the monitoring electrodes through another conductive path defined by the fluid; and
    a power source for exciting one or more of the excitation electrodes for determining the electrical resistance of the fluid.

11. The assembly of claim 10, further comprising a plurality of rings and a plurality of central electrodes.

12. The assembly of claim 11, wherein the plurality of rings are coupled to a plurality of rails and the plurality of central electrodes are coupled to a central rail.

13. The assembly of claim 12, wherein each of the plurality of rails and the central rail comprises an insulator.

14. The assembly of claim 11, wherein the plurality of rings comprises two sets of rings, and wherein each of the two sets of rings comprises two guard rings and a measurement ring.

15. The assembly of claim 14, wherein the two guard rings are equidistant from the measurement ring.

16. A method comprising:
    transmitting power from a power source to an excitation electrode coupled to a non-conductive frame through which fluid is flowing, wherein the non-conductive frame comprises the excitation electrode and a monitoring electrode, and wherein a central electrode is positioned in the fluid for conductively coupling the excitation electrode and the monitoring electrode through a conductive path defined by a fluid;

measuring, by an electronics unit, a current and a first voltage at the excitation electrode;

measuring, by the electronics unit, a second voltage at the monitoring electrode;

determining, by a computing device, one or more electrical resistances associated with the fluid based on the current, the first voltage, and the second voltage; and determining, by the computing device and based on the one or more electrical resistances associated with the fluid, whether the fluid comprises oil, water, or gas.

17. The method of claim 16, further comprising determining, by the computing device, a composition, a flow velocity, a quantity of a fluid component, and a flow regime of the fluid.

18. The method of claim 16, further comprising transmitting, by a telemetry unit, the current, the first voltage, and the second voltage from the electronics unit to the computing device.

\* \* \* \* \*